US011864816B2

(12) United States Patent
Brooke (10) Patent No.: US 11,864,816 B2
(45) Date of Patent: Jan. 9, 2024

(54) ELECTROSURGICAL INSTRUMENT WITH ILLUMINATION ELEMENT

(71) Applicant: Gerard Michael Brooke, Tetbury (GB)

(72) Inventor: Gerard Michael Brooke, Tetbury (GB)

(73) Assignee: Gerard Michael Brooke, Tetbury (GB)

( * ) Notice: Subject to any disclaimer, the term of this patent is extended or adjusted under 35 U.S.C. 154(b) by 317 days.

(21) Appl. No.: 16/622,328

(22) PCT Filed: Apr. 18, 2018

(86) PCT No.: PCT/GB2018/051013
§ 371 (c)(1),
(2) Date: Dec. 13, 2019

(87) PCT Pub. No.: WO2018/203030
PCT Pub. Date: Nov. 8, 2018

(65) Prior Publication Data
US 2020/0197074 A1 Jun. 25, 2020

(30) Foreign Application Priority Data
May 5, 2017 (GB) ...................................... 1707193

(51) Int. Cl.
*A61B 18/14* (2006.01)
*A61B 90/30* (2016.01)
*A61B 18/00* (2006.01)

(52) U.S. Cl.
CPC .......... *A61B 18/1402* (2013.01); *A61B 90/30* (2016.02); *A61B 2018/0091* (2013.01);
(Continued)

(58) Field of Classification Search
CPC ................ A61B 18/1402; A61B 90/30; A61B 2018/00589; A61B 2018/00601; A61B 2018/0091; A61B 2218/008
See application file for complete search history.

(56) References Cited

U.S. PATENT DOCUMENTS

| 4,562,838 A | 1/1986 | Walker |
| 4,687,295 A * | 8/1987 | Koishi ............... G02B 6/02033 385/143 |

(Continued)

FOREIGN PATENT DOCUMENTS

| GB | 2524742 | 10/2015 |
| WO | WO2004054626 | 7/2004 |

(Continued)

OTHER PUBLICATIONS

International Search Report and Written Opinion of the International Searching Authority in related application PCT/GB2018/051013, dated Jun. 15, 2018, 9 pages.

*Primary Examiner* — Eun Hwa Kim
*Assistant Examiner* — Catherine Premraj
(74) *Attorney, Agent, or Firm* — Bochner PLLC; Andrew D. Bochner (57) ABSTRACT

An electrosurgical instrument (10) comprising a housing (12) having an elongate main body (14) extending in an axial direction, and a grippable member (32); an implement (16) fixed relative to and projecting from a forward region of the main body (14); a smoke evacuation passage defined within the main body (14) and extending from an inlet proximal to the implement (16); and an electrical conductor housed within the housing (12) for supplying an electrosurgical current to the implement (16). A separate elongate illumination element (62) is also provided which is engagable with the housing (12), the housing (12) including an axial retaining element (54) on the main body (14) for releasably engaging the elongate illumination element (62). The grippable member (32) is then slidably connected to the main body (14) over the elongate illumination element (62) such that the axial position of the grippable member (32) relative (Continued)

to the main body (14) may be adjusted in use without altering a position of the elongate illumination element (62).

13 Claims, 4 Drawing Sheets

(52) U.S. Cl.
CPC .............. *A61B 2018/00589* (2013.01); *A61B 2018/00601* (2013.01); *A61B 2218/008* (2013.01)

(56) References Cited

U.S. PATENT DOCUMENTS

| | | | | |
|---|---|---|---|---|
| 5,246,440 | A * | 9/1993 | Van Noord | A61B 18/1402 |
| | | | | 606/39 |
| 6,099,525 | A * | 8/2000 | Cosmescu | A61B 18/00 |
| | | | | 604/35 |
| 6,635,034 | B1 * | 10/2003 | Cosmescu | A61M 1/774 |
| | | | | 604/289 |
| 2008/0147058 | A1 * | 6/2008 | Horrell | A61B 90/30 |
| | | | | 606/37 |
| 2011/0112530 | A1 * | 5/2011 | Keller | A61B 18/14 |
| | | | | 606/42 |
| 2014/0303449 | A1 | 10/2014 | Balog | |
| 2015/0148596 | A1 | 5/2015 | Gitman | |

FOREIGN PATENT DOCUMENTS

| | | |
|---|---|---|
| WO | WO2014189471 | 11/2014 |
| WO | WO2017001379 | 1/2017 |

\* cited by examiner

ELECTROSURGICAL INSTRUMENT WITH ILLUMINATION ELEMENT

The present invention relates to an electrosurgical instrument having an illumination element, particularly but not necessarily exclusively for use at different depths within a patient's body. The invention further relates to an electrosurgical instrument capable of receiving an illumination element, and to a corresponding illumination element.

Electrosurgical instruments normally comprise a main body portion which is held by a surgeon and which contains an electrosurgical power supply, and an electrosurgical implement projecting from the forward end thereof to which electrosurgical current is applied via the power supply. The power supply may include some control circuitry or may be a power line which is arranged to be connected to a remotely located control circuitry in use, for example, being controllable via a foot pedal.

Such instruments are typically selectively operable to effect cutting or coagulation of tissue by the application of high frequency current via the electrosurgical implement which acts as an electrode.

In some applications, the instrument may be required to be used for different tasks, relating to different depths within a patient's body. One way of providing such an arrangement is to allow the position of the tip of the electrode to be variable with respect of a gripping portion of the instrument.

Illumination of a tissue site is problematic, however. The provision of inbuilt lighting on the electrosurgical implement can increase the bulk and cost of production, making the instrument more unwieldly. Clip-on lighting devices are available, but these also have a tendency to block the operative site, or are ineffective at providing sufficient illumination of the operative site.

The present invention seeks to provide an electrosurgical instrument with an illumination element which obviates or reduces the above-referenced problems.

According to a first aspect of the invention, there is provided an electrosurgical instrument comprising: a housing having an elongate main body extending in an axial direction, and a grippable member; an implement fixed relative to and projecting from a forward region of the main body; a smoke evacuation passage defined within the main body and extending from an inlet proximal to the implement; an electrical conductor housed within the housing for supplying an electrosurgical current to the implement; and an elongate illumination element engagable with the housing; the housing including an axial retaining element on the main body for releasably engaging the elongate illumination element, the grippable member being slidably connected to the main body over the elongate illumination element such that the axial position of the grippable member relative to the main body may be adjusted in use without altering a position of the elongate illumination element.

The ability to illuminate an operative area without the illumination means blocking either the implement itself or a slidable member of the instrument allows a surgeon to have a well-lit view of the operative area without compromising the maneuverability of the electrosurgical instrument. This significantly reduces the risk of accidental damage to the patient during the procedure.

Preferably, the implement may be an electrode.

In one preferred embodiment, the illumination element may include a light source and an elongate light-transmissible body portion, the light-transmissible body portion being engagable with the axial retaining element of the housing.

The provision of an elongate body beneficially allows the illumination element to be supported along a large proportion of the axial extent of the instrument. This allows the lighting element to be well supported, limiting the likelihood of displacement of the illumination element in use.

Preferably, the light-transmissible body portion may be formed from a poly(methyl methacrylate).

A poly(methyl methacrylate) body portion, preferably being coated with a highly internally reflective coating, allows for extended transmission of the light from the light source along the length of the instrument, which in turn simplifies many of the constructional aspects of the instrument.

Optionally, the illumination element may be engagable with the axial retaining element such that the light source is at or adjacent to a rear portion of the main body. Preferably, the said light source may be a light-emitting diode.

By spacing the light source from the active operative end of the instrument, there is no risk of the light source becoming heating and causing accidental pain or damage to the patient during electrosurgery.

The illumination element may comprise an angled portion at a proximal end of the light-transmissible body portion, in which case the main body may include a stop against which the angled portion of the illumination element can in use abut when engaged with the axial retaining element, a length of the light-transmissible body portion being less than a distance from the stop to a distalmost end of the implement to prevent in use overextension of the illumination element beyond the end of the implement.

The limiting of the axial projection of the tip of the illumination element limits the chance that the tip will contact the operative site in use, which could be an infection risk. Furthermore, the curvature of the illumination element can also allow the mounting of a proximal end of the illumination element at various different angles, which may be beneficially particularly where different surgeons using the instrument are left- or right-handed.

The illumination element may comprise an onboard power source, which may be a battery unit housed in a proximal end chamber of the illumination element. Alternatively, the illumination element may be mains electricity powered.

The provision of an onboard battery unit as part of a removable illumination element ensures that the electrosurgical instrument itself can be manufactured without the provision of its own battery unit. This is of particular relevance in regulatory environments in which the supply of battery-based power sources is strictly monitored.

Preferably, the axial retaining element may define a receiving channel within which the illumination element is at least in part receivable.

A receiving channel provides a simple mechanism by which an elongate illumination element can be engaged with the main body of the housing. For example, an appropriate channel could be readily moulded into the main body at the point of manufacture.

The illumination element may be slidably receivable in the receiving channel from a proximal end of the housing.

The slidable insertion of the illumination element into a receiving channel limits the overall volume of the instrument in use, whilst also being a straightforward method of installing and adjusting the illumination during an operative procedure.

Preferably, the axial retaining element may comprise a front collar, elongate groove, and rear collar which collectively define the receiving channel.

Front and rear collars can provide ample support for an elongate lighting element, whilst an open central groove may allow at least some light emission, improving the overall lighting effect at or around the operative site.

The grippable member may comprise a lower portion which is in use slidable over the receiving channel of the axial retaining element without blocking the said receiving channel, in which case, the lower portion of the grippable member may act as a secondary retaining means for the illumination element.

The lower portion of the grippable member may beneficially be formed so as to effectively form an outer boundary for the receiving channel which is spaced apart from the main body. This not only further prevents accidental lateral ejection of the illumination element from the main body, but also ensures that there is no rubbing between the illumination element and the grippable member as the grippable member slides along the housing, which could potentially damage the body portion of the illumination element.

According to a second aspect of the invention, there is provided an electrosurgical instrument comprising: a housing having an elongate main body extending in an axial direction, and a grippable member; an implement fixed relative to and projecting from a forward region of the main body; an electrical conductor housed within the housing for supplying an electrosurgical current to the implement; and the housing including an axial retaining element on the main body for releasably engaging an elongate element therein, the grippable member being slidably connected to the main body over the axial retaining element such that the axial position of the grippable member relative to the main body may be adjusted in use.

The provision of an axial retaining element on an electrosurgical instrument beneficially allows an illumination element to be readily connected thereto without altering the overall volume of the instrument in the operative region. This advantageously allows for a removable illumination element to be provided without limiting the operative control of the instrument.

The axial retaining element may define a receiving channel within which an illumination element is at least in part receivable, in which case the axial retaining element may comprise a front collar, elongate groove, and rear collar which collectively define the receiving channel. The grippable member may comprise a lower portion which is in use slidable over the receiving channel of the axial retaining element without blocking the said receiving channel.

According to a third aspect of the invention, there is provided an illumination element for an electrosurgical instrument comprising an elongate light-transmissible body portion and a proximal end portion including a light source and a powering means for the light source, the body portion and end portion being connected via an intermediate angled portion such that illumination generated by the light source is transmissible from the proximal end portion via the intermediate angled portion to a distal end of the body portion.

A dedicated elongate illumination element can be manufactured which can be readily engaged with an electrosurgical instrument to provide illumination which is fixed relative to an implement thereof, without increasing the overall volume of the instrument.

In a preferred embodiment, the light-transmissible body portion may be formed from a poly(methyl methacrylate). Furthermore, the light source may be a light emitting diode. The illumination element may comprise an onboard power source, which may be a battery unit housed in a proximal end chamber of the illumination element. Alternatively, the illumination element may be mains electricity powered.

According to a fourth aspect of the invention, there is provided an electrosurgical instrument comprising: a housing having an elongate main body extending in an axial direction; an implement fixed relative to and projecting from a forward region of the main body; an electrical conductor housed within the housing for supplying an electrosurgical current to the implement; and the housing including an axial retaining element on the main body for releasably engaging an elongate element therein at a fixed distance relative to the implement.

Whilst an electrosurgical instrument is described having a slidable grippable member, it will be appreciated that the present invention could be extended for any electrosurgical instrument for which it would be useful to have an illumination element which is positionally fixed relative to the implement, in order to provide low-profile illumination of an operative site.

The invention will now be more particularly described, by way of example only, with reference to the accompanying drawings, in which:

FIG. 2a(i) shows a plan view of the electrosurgical instrument of FIG. 1a;

FIG. 2a(ii) shows a cross-section through the electrosurgical instrument taken through line A-A of FIG. 2a(i);

FIG. 2b(i) shows a plan view of the electrosurgical instrument of FIG. 1b;

FIG. 2a(ii) shows a cross-section through the electrosurgical instrument taken through line B-B of FIG. 2b(i);

Figures 1A, 1B:
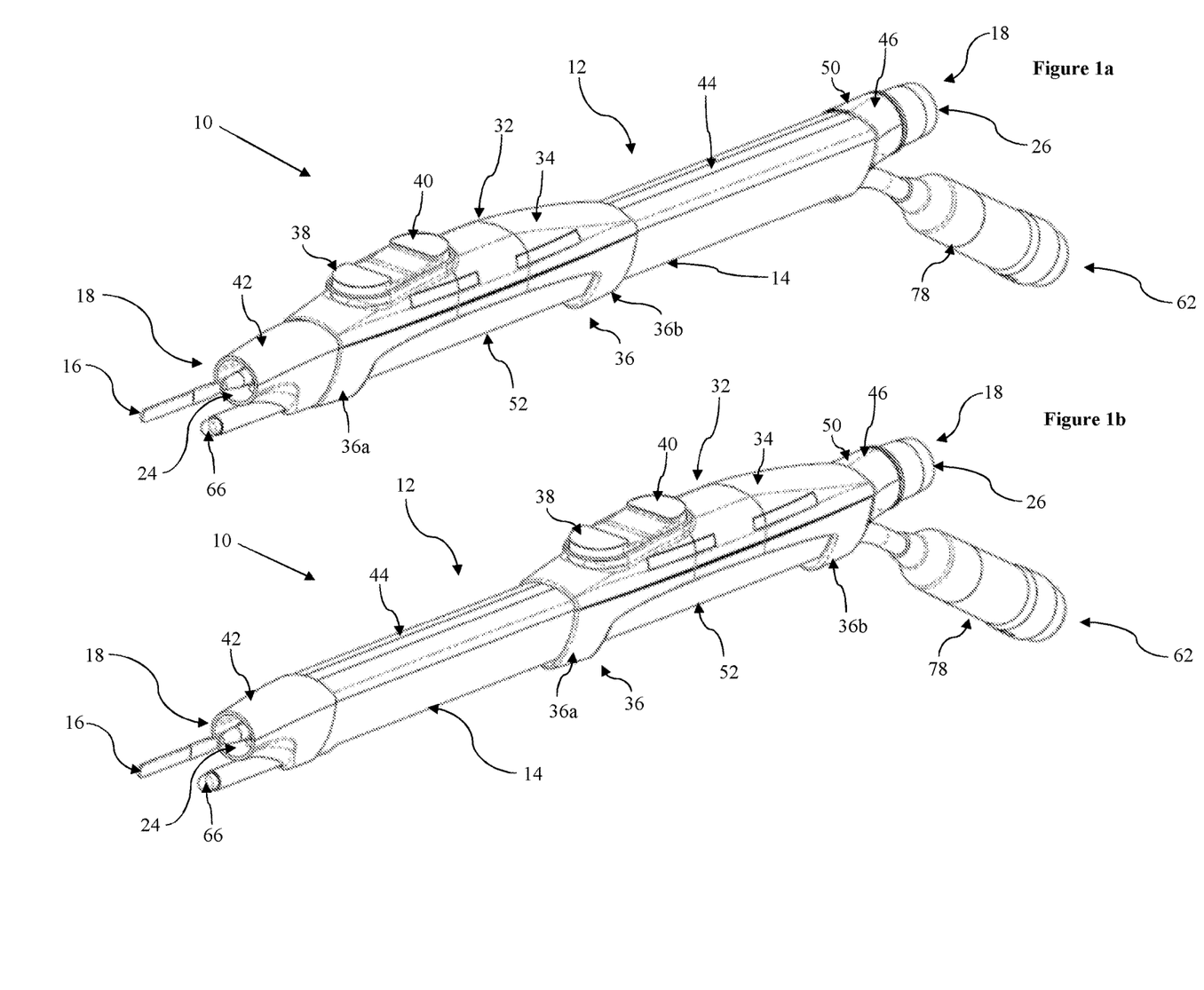
FIG. 1a shows an isometric representation of one embodiment of an electrosurgical instrument in accordance with the first aspect of the invention, a grippable member thereof being in a first, advanced condition.
FIG. 1b shows an isometric representation of the electrosurgical instrument of FIG. 1a, the grippable member thereof being in a second, retracted condition.

Referring to FIGS. 1a and 1b, there is shown an electrosurgical instrument, indicated globally at 10, which is suitable for use in electrosurgery of a patient at different operative depths.

The electrosurgical instrument 10 includes a housing 12 which comprises an elongate main body 14 which extends in an axial direction. An implement 16 for electrosurgery is provided at a forward end 18 of the electrosurgical instrument 10, that is, an end of the instrument which is directed towards a patient during an electrosurgical procedure, and is the end which is distalmost to an operator of the electrosurgical instrument 10. The electrosurgical instrument 10 could be a monopolar or bipolar electrosurgical instrument, by way of example only.

The implement 16 is preferably an electrosurgical electrode, and is fixed relative to and projecting from a forward region of the main body 14, and the implement 16 may be preferably located in a mounting feature 20, which may preferably be a dedicated moulded mounting, of the forward end 18 of the housing 12. This can be seen in particular in FIGS. 2a(i), 2a(ii), 2b(i), and 2b(ii), which indicate cross-sections through the housing 12.

The main body 14 is preferably provided a cylindrical or substantially circular tubular body having a central bore 22 extending therethrough. The central bore 22 therefore defines a smoke evacuation passage within the main body 14, and is used to remove any smoke and/or fumes produced during an electrosurgical procedure. The central bore 22 and therefore the smoke evacuation passage extends from an inlet 24 which is proximal the implement 16 to an outlet 26 which is at an opposite, rearward, end 28 of the housing 12.

Figure 2A:
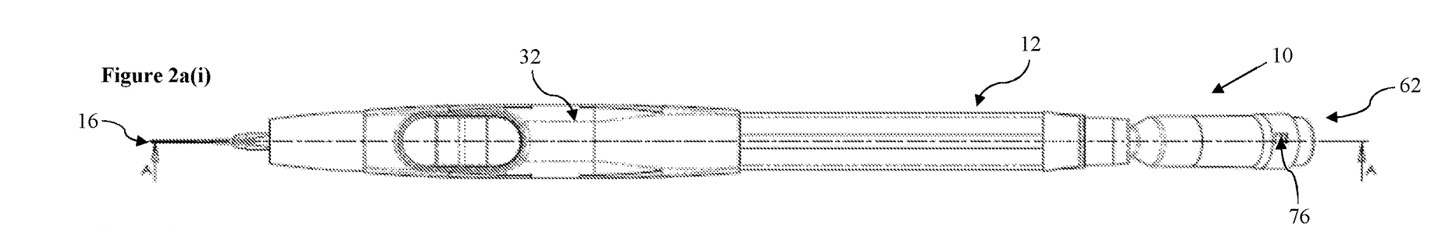
Figures 2A, 2B:
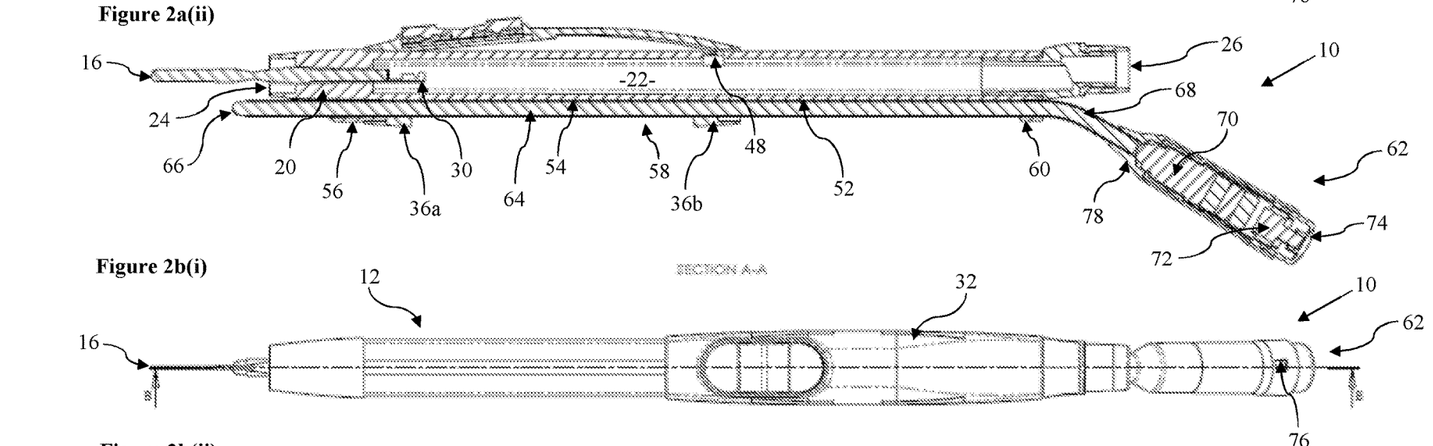
Figure 2B:
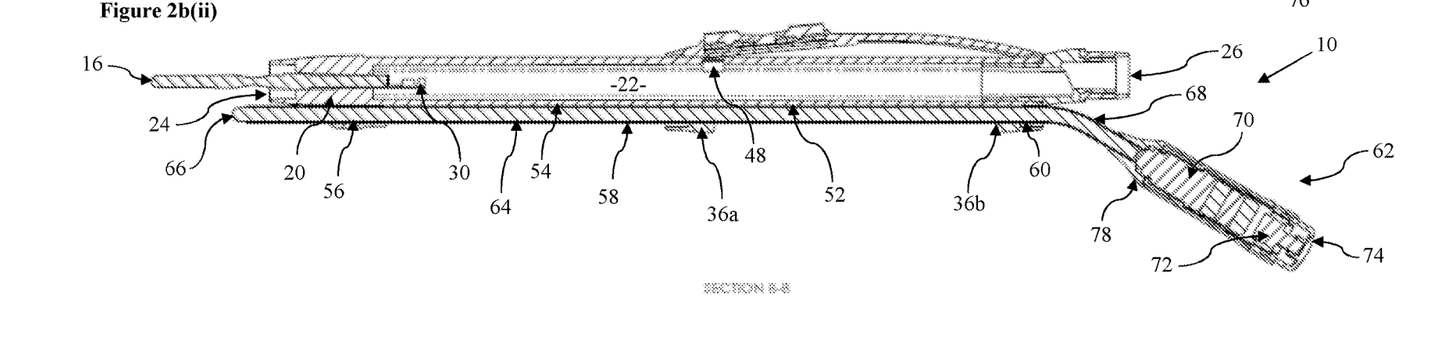

Preferably, the inlet 24 is formed so as to surround or substantially the implement 16 and has an annular cross-section. The outlet 26 is arrange to be connected in use to a, preferably flexible, tubing through which a suction vacuum may be provided. An electrical conductor is also typically provided inside the central bore 22, to provide an electrical current to the implement 16; a connector 30 of the implement 16 is illustrated in FIGS. 2a(ii) and 2b(ii) to which an appropriate electrical connector, such as a conductive wire, may be connected.

The electrical conductor may be a wire or a circuit applied to a membrane within the housing 12. Flexible circuits could be utilised, such as single metal layered, double sided, multilayer, and/or rigid flex circuits.

A grippable member 32 is also provided so as to be slidably connected or connectable to the main body 14 of the housing 12, such that an axial position of the grippable member 32 relative to the main body 14 may be adjusted in use. The grippable member 32 includes an upper portion 34 which is intended to be held by a forefinger of a user, such as a surgeon, in use (in a "pen-like" grip). The grippable member 32 also includes a lower portion 36 which extends around the opposing surface of the housing 12 and retains the grippable member 32 thereon.

In the present embodiment, the lower portion 36 is formed having first and second lower engagement members 36a, 36b which are axially spaced apart from one another on the grippable member 32, and which provide engagement of the grippable member 32 on the housing 12 at both ends of the grippable member 32.

At least one switch, and preferably first and second switches or buttons 38, 40 may be provided on a surface of the upper portion 34 of the grippable member 32, which may be respectively used for activating coagulation and/or cutting functionality of the electrosurgical instrument 10. The first and second switches or buttons 38, 40 are arranged to be operable by a user of the electrosurgical instrument 10, in use.

The grippable member 32 and main body 14 may be preferably provided with complementary engagement formations which may provide indexed positions for the grippable member 32 in the axial direction of the main body 14. Such indexing positions may be provided by a track on at least one side of the main body 14 of the housing, with a complementarily profiled tooth being located on the grippable member 32.

The grippable member 32 is preferably formed as a carriage which is movable along the axial direction of the main body 14 on the housing 12. On application of a sufficient force, the carriage is slidable along the main body 14. The main body 14 may be formed so as to have a front portion 42, a middle portion 44 along which the grippable member 32 is movable, and a rear portion 46. The grippable member 32 may be movable between a rearmost or proximal position in which the grippable member 32 abuts or is adjacent to the rear portion 46, and a foremost or distal position in which the grippable member 32 abuts or is adjacent to the front portion 42. It will be appreciated that the grippable member 32 could be arranged so as to only be secured at certain positions along the middle portion 44 of the main body 14, or could be freely movable along the middle portion 44.

In the present embodiment, the grippable member 32 may be formed having a rounded or similarly ergonomic profile, as can be best seen in FIGS. 2a(ii) and 2b(ii). Preferably, the grippable member 32 is sized to span at least half of the length of the middle portion 44 of the main body 14. An access aperture 48 may be provided at or close to a centre of the middle portion 44 of the main body 14 so as to always be covered by part of the grippable member 32 in use. Such an access aperture 48 may be used to provide a via into the central bore 22 of the housing 12, thereby ensuring that an electrical connection between the implement 16 and/or electrical connector can be made to the first and/or second switches or buttons 38, 40 of the grippable member 32.

An evacuation means, such as an evacuator, may be couplable to the outlet 26 of the smoke evacuation passage at or adjacent to the rear portion 46 of the electrosurgical implement 10, particularly but not necessarily exclusively via a flexible tubing. The evacuation means is able to encourage smoke and/or fumes to be evacuated from the central bore 22, and other debris created during the electrosurgical process may also be removed in this manner.

The rear portion 46 of the electrosurgical implement 10 may be provided with a kinked portion 50 which is laterally offset from the main body 14 of the housing 12. This may improve an accessibility of the rear portion 46 for connection to a said flexible tubing.

The housing 12 includes on one longitudinal surface thereof, preferably a lower surface 52 with respect to the grippable member 32, an axial retaining element 54 which is engagable with an elongate element. The axial retaining element 54 here comprises a front collar 56 which is positioned at or adjacent to the front portion 42 of the main body 14, an elongate groove or recess 58 which preferably extends along at least a majority of, and preferably the full extent of, the middle portion 44 of the main body 14, and a rear collar 60 which is positioned at or adjacent to the rear portion 46 of the main body 14.

The front collar 56, elongate groove 58, and rear collar 60 collectively define a receiving channel within which an elongate element is receivable and retainable against the main body 14 of the housing 12. The lower portion 36 of the grippable member 32 is formed such that there is no interference or impingement within the receiving channel of the axial retaining element 34, thereby allowing the grippable member 32 to slide along the middle portion 44 of the main body 14 freely.

The first and second lower engagement members 36a, 36b may be mutually engagable with the respective front and rear collars 56, 60 to effectively lock the grippable member 32 in position at the foremost and rearmost positions. The first and second lower engagement members 36a, 36b may be formed having receiving slots within which the front and rear collars 56, 60 are receivable, as can be seen in FIGS. 2a(ii) and 2b(ii).

It will be appreciated that the axial retaining element 54 could be formed so as to define a continuous bounded channel along the axial extent of the main body 14, and/or could be provided as a continuous open groove within which an elongate element may snap fit or engage frictionally. One or more detents could be provided in such a groove to retain the axial position of the elongate element. Other similar arrangements will be evident to the skilled person.

An illumination element 62 or similar illumination means is also provided which is engagable with the axial retaining element 54 of the housing 12. In the present embodiment, the illumination element 62 is provided so as to have an elongate body portion 64, which is preferably formed as a rod-like or wand-like light-transmissible body, and may be formed from an acrylic plastics material, such as poly (methyl methacrylate). The light-transmissible body may be formed so as to have a coating to prevent light emission other than at a tip 66 of the body portion 64, which is in use at or adjacent to the implement 16.

At least a majority of body portion 64 may be linear, having a uniform width or diameter which is receivable within the channel of the axial retaining element 54. At a proximal, rear end of the illumination element 62, there may be an angled, necked, crooked or curved portion 68 which in use bends away or diverges from the main body 14 of the electrosurgical instrument 10.

The illumination element 62 includes a light source 70, which is preferably provided as an illumination element positioned at or adjacent to the proximal, rear end of the illumination element 62. Preferably, the light source 70 is provided as a light-emitting diode, which is coupled to the light transmissible body portion 64 so as to direct light towards and out of the tip 66 of the illumination element 64.

The light source 70 is provided in communication with a power source. In the depicted embodiment, the illumination element 62 includes an onboard battery unit 72 which provides electrical power to the light-emitting diode. The battery unit 72 is accessible via a cap 74 of the illumination element 62, to allow the battery unit 72 to be replaced. Alternatively, the battery unit 72 could be rechargeable from a mains electrical supply. It will, of course, be appreciated that the illumination element 62 could readily be provided so as to have a mains electricity connector and/or socket, or could be provided so as to be connectable to an external and/or portable power supply.

The illumination element 62 may be provided with an activation switch 76 which allows the user to activate or deactivate the light source 70. Preferably, the activation switch 76 is provided at the proximal rear end of the illumination element 62, which may be provided at or adjacent to the battery unit 72.

Figures 3A, 3B:
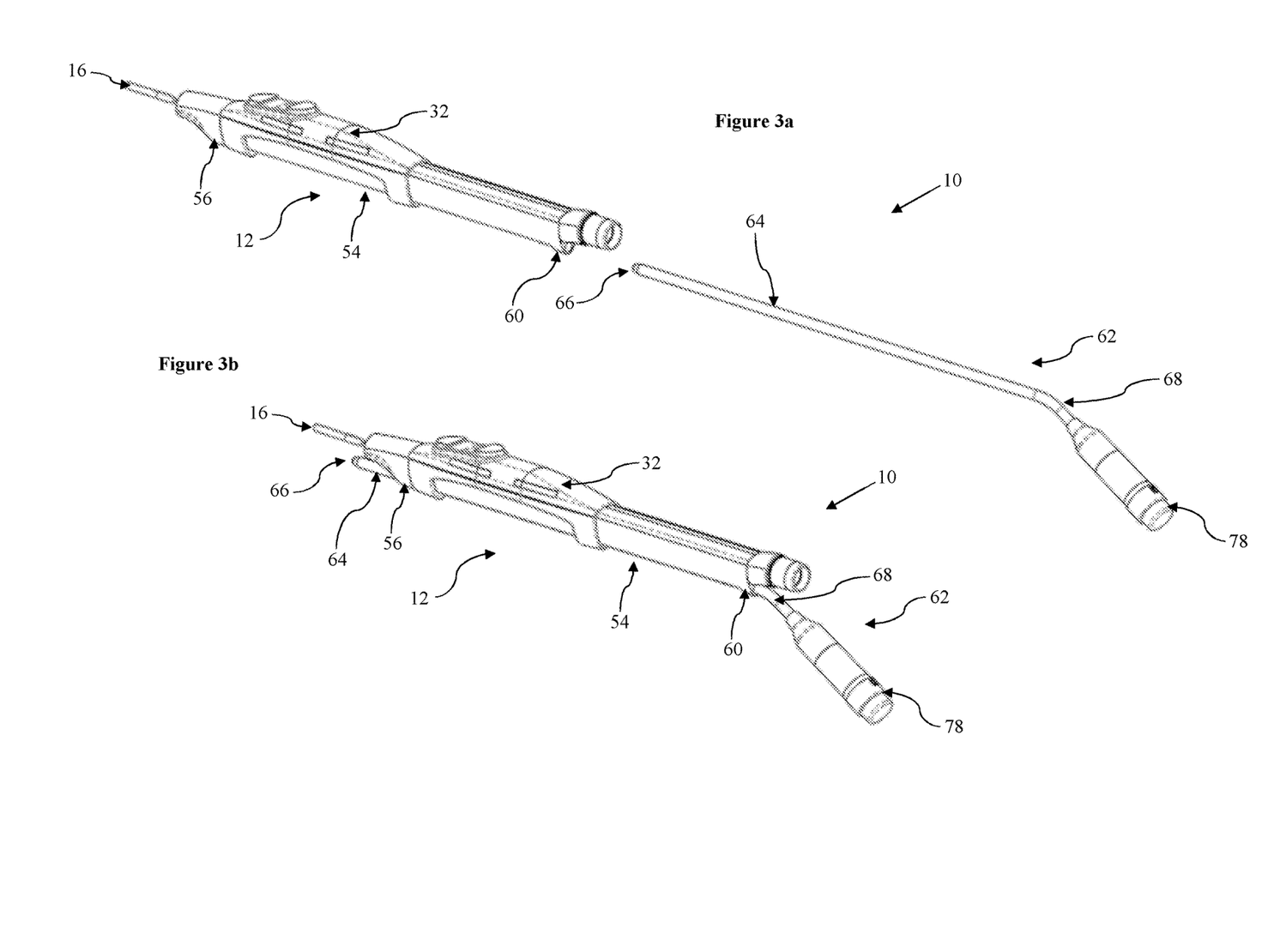
FIG. 3a shows an isometric representation of the electrosurgical instrument of FIG. 1a, with the illumination element removed from the axial retaining element thereof.
FIG. 3b shows an isometric representation of the electrosurgical instrument of FIG. 3a, the illumination element being inserted into the axial retaining element thereof.

An exemplary engagement between the housing 12 and the illumination element 62 is illustrated in FIGS. 3a and 3b. To engage the illumination element 62 with the housing 12, the elongate body portion 64 is introduced towards and into the axial retaining element 54, preferably from the proximal rear end thereof, as shown in FIG. 3a. The entire illumination element 62 can then be urged along the longitudinal extent of the main body 14 until a desired position of the illumination element 62 is achieved, relative to the implement 16. The engaged arrangement of the electrosurgical instrument 10 is shown in FIG. 3b. Preferably, the illumination element 62 is introducible into the axial retaining element 54 in a slidable manner.

An axial position of the elongate body portion 64 of the illumination element 62 is preferably held within the axial retaining element 54 by a frictional or interference fit, and therefore no dedicated clips or connectors are required. Instead, the main body 14 is formed so as to directly receive the illumination element 62. However, one or more positioning elements could be provided, such as detents, which assist with retention of the illumination element in specific axial positions relative to the implement 16.

As can be seen, the receiving of the elongate body portion 64 fully within the channel of the axial retaining element 54 ensures that the grippable member 32 is slidable along the middle portion 44 of the main body 14 without colliding with and/or displacing the illumination element 62. The lower portion 36 of the grippable member 32 even serves to act as a secondary retainer or retaining means to prevent accidental disengagement of the illumination element 62 from the main body 14 of the housing 12.

The angled portion 68 of the illumination element 62 may be positioned so as to act as a stop against overinsertion of the elongate body 64 into the axial retaining element 54. This may prevent the tip 66 of the illumination element from being positioned in advance of the implement 16, ensuring that the tip 66 is not the first point of contact with a patient in use, which could interfere with an electrosurgical procedure.

Furthermore, the angled portion 68 of the illumination element 62 may be repositioned relative to the longitudinal axis of the housing 12 by rotation of the illumination element 62. The proximal end chamber 78 of the illumination element 62 may be moved so as to project in-line with a vertical plane through the electrosurgical instrument 10, as indicated by lines A-A and B-B in FIGS. 2a(i) and 2b(i) respectively. Alternatively, the proximal end chamber 78 may be aligned at an angle out of the said plane, either in a right- or left-hand direction. This may allow the proximal end chamber 78 to be positioned out of the way of the user's arm in use.

Figure 4A:
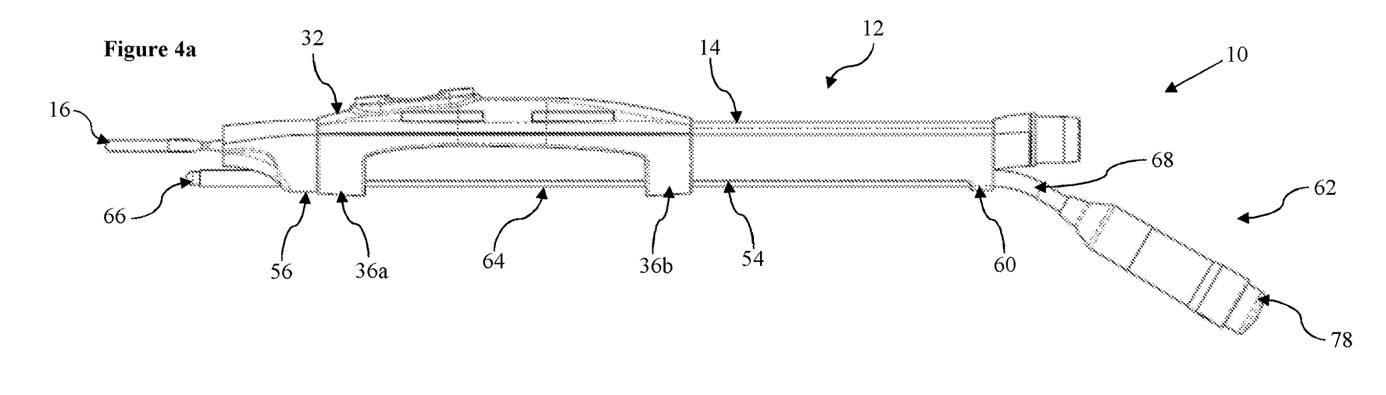
FIG. 4a shows a side view of the electrosurgical instrument of FIG. 1a, with the illumination element being in an in use first, advanced condition.

FIG. 4a shows the illumination element 62 in position for the electrosurgical instrument 10. In this first condition, the tip 66 of the illumination element 62 is advanced as far towards the distal end of the electrosurgical instrument 10 as is possible, as the angled portion 68 has acted as a stop.

Figure 4B:
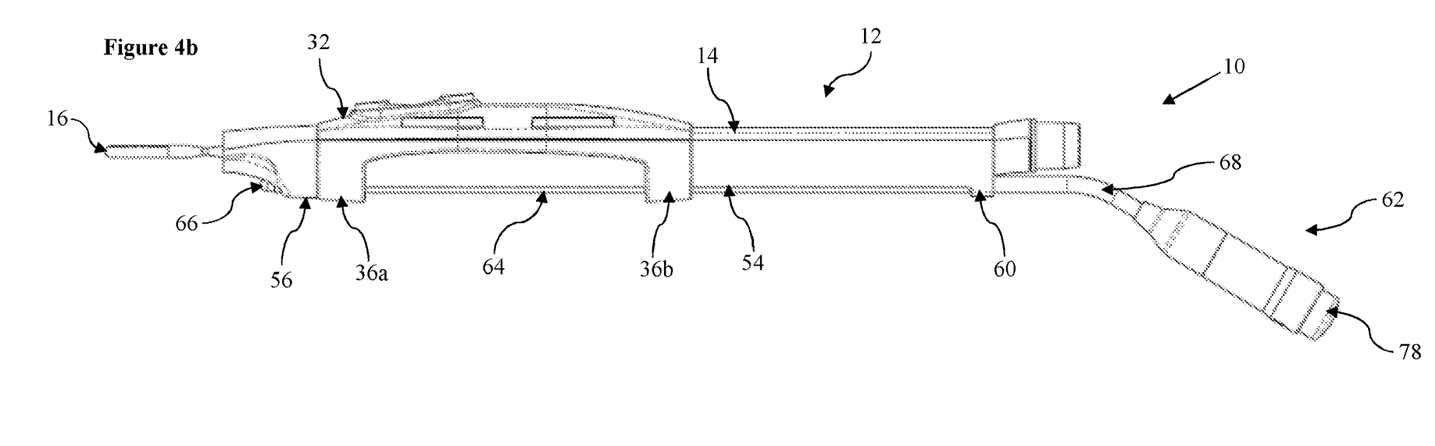
FIG. 4b shows a side view of the electrosurgical instrument of FIG. 4a, with the illumination element being in an in use second, retracted condition.

In FIG. 4b, a second, retracted condition is illustrated, in which the tip 66 of the illumination element 62 is close to or within the front collar 56 of the axial retaining element 54. The frictional or interference engagement between the illumination element 62 and the axial retaining element 54 ensures that, without a significant pulling force on the illumination element 62 by the user at the proximal end, the illumination element 62 will not be displaced in use.

In use, a user is able to grasp the grippable member 32 between their fingers and apply a force along a longitudinal direction of choice, dependent upon the desired application of use. The user thereby selects a desired position of the grippable member 32 between at least a foremost position, whereby the distance between a distalmost end of the implement 16 and a front of the grippable member 32 is minimised, as is the case in FIG. 1a, and a rearmost position wherein the distance between the distalmost end of the implement 16 and the front of the grippable member is maximised, as shown in FIG. 1b. This movement is performed along the middle portion 44 of the main body 14 and between the front portion 42 and rear portion 46 of the main body 14.

The movement of the grippable member 32 effectively alters a usable length of the electrosurgical instrument 10, the usable length being the distance from the distalmost end of the implement 16 and the gripping position, that is, the grippable member 32.

The implement 16 of the electrosurgical instrument 10 creates smokes during operation which can be a health hazard to the surgeon or other people in the vicinity of the smoke and may be considered toxic or unpleasant. The smoke evacuation means may be activated during use which causes smoke at the implement 16 to be drawn through the central bore 22 and out of the outlet 26 located at the rear of the main body 14 of the housing 12. The implement 16 may be provided with a controllable smoke passage obstructer which enables the smoke evacuation passage to be selectably blocked and/or choked during operation, if desired.

This arrangement advantageously allows the user of the electrosurgical instrument 10 to readily advance or retract the illumination element 62 so as to provide contextually appropriate lighting during an electrosurgical operation. Advancement of the tip 66 of the illumination element 62 towards the distalmost end of the implement 16 is likely to improve illumination of the patient operative site, whilst reducing the surgeon's maneuverability with the electrosurgical instrument 10. In such a case, simple retraction of the illumination element 62 is useful.

Once a particular position of the tip of the illumination element 62 has been chosen, however, the relative position of the implement 16 and illumination element 62 remains unchanged unless the user alters the position of the illumination element 62. This allows the grippable member 32 to be used to alter the effective useable length of the electrosurgical instrument 10 without altering the lighting capability at or around the implement 16. Furthermore, since the illumination element 62 is largely held captive by the electrosurgical instrument 10, there is no significant alteration to the overall volume of the electrosurgical instrument 10 by provision of the illumination element 62.

Whilst the implement herebefore described is an electrode, it will be appreciated that there are several different classes of electrosurgical instrument with which the present invention could be utilised, including but not limited to forceps or electrosurgical pencils. The smoke evacuation passage of the electrosurgical implement could feasibly be dispensed with in certain embodiments of the invention.

In such an arrangement it may therefore be possible to provide an electrosurgical instrument comprising a housing having an elongate main body extending in an axial direction, an implement fixed relative to and projecting from a forward region of the main body, an electrical conductor housed within the housing for supplying an electrosurgical current to the implement, and the housing including an axial retaining element on the main body for releasably engaging an elongate element therein at a fixed distance relative to the implement. In this arrangement, it may be possible to eliminate the grippable member, and therefore provide any electrosurgical instrument with an axial retaining element which can grip or otherwise releasably engage an illumination element with the body thereof. This maintains the relative position of the illumination element to the implement of the electrosurgical instrument in use.

It is therefore possible to provide an electrosurgical instrument which has an illumination element which is releasably engagable with a main body of the instrument so as to be fixed relative to an implement thereof, whilst also allowing the use of a slidable gripping carriage which allows the alteration of the length of the electrosurgical instrument during an operative procedure. This beneficially improves the illumination of an operative site of a patient without inhibiting the range of movement of the instrument.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention as defined herein.

The invention claimed is:

1. An electrosurgical instrument comprising:
a housing having
an elongate main body extending in an axial direction, and
a grippable carriage;
an implement fixed relative to and projecting from a forward region of the main body;
a smoke evacuation passage defined within the main body and extending from an inlet proximal to the implement;
an electrical conductor housed within the housing for supplying an electrosurgical current to the implement; and
an elongate illuminator engagable with the housing, the illuminator including a light source and an elongate light-transmissible body portion;
the housing including an axial retainer on the main body, the light-transmissible body portion of the illuminator being engagable with the axial retainer of the housing,
the grippable carriage being formed as a slidable carriage connected to the main body, a lower portion of a grippable member being receivable over the elongate illuminator when engaged with the axial retainer such that the axial position of the grippable carriage relative to the main body may be adjusted in use without altering a position of the elongate illuminator,
wherein at least one switch is provided on a surface of an upper portion of the grippable member such that a distance between the implement and the at least one switch is alterable when the axial position of the grippable carriage is adjusted; and
wherein the at least one switch is associated with electrosurgical function of the implement.

2. The electrosurgical instrument as claimed in claim 1, wherein the implement is an electrode.

3. The electrosurgical instrument as claimed in claim 1, wherein the light-transmissible body portion is formed from a poly(methyl methacrylate).

4. The electrosurgical instrument as claimed in claim 1, wherein the illuminator is engagable with the axial retainer such that the light source is at or adjacent to a rear portion of the main body.

5. The electrosurgical instrument as claimed in claim 1, wherein the illuminator comprises an angled portion at a proximal end of the light-transmissible body portion.

6. The electrosurgical instrument as claimed in claim 5, wherein the main body includes a stop against which the angled portion of the illuminator can in use abut when engaged with the axial retainer, a length of the light-transmissible body portion being less than a distance from the stop to a distalmost end of the implement to prevent in use overextension of the illuminator beyond the end of the implement.

7. The electrosurgical instrument as claimed in claim 1, wherein the illuminator comprises an onboard power source such as a battery unit housed in a proximal end chamber of the illuminator.

8. The electrosurgical instrument as claimed in claim 1, wherein the illuminator is mains electricity powered.

9. The electrosurgical instrument as claimed in claim 1 wherein the axial retainer defines a receiving channel within which the illuminator is at least in part receivable.

10. The electrosurgical instrument as claimed in claim 9, wherein the illuminator is slidably receivable in the receiving channel from a proximal end of the housing.

11. The electrosurgical instrument as claimed in claim 9, wherein the axial retainer comprises a front collar, elongate groove, and rear collar which collectively define the receiving channel.

12. The electrosurgical instrument as claimed in claim 9, wherein the lower portion is in use slidable over the receiving channel of the axial retainer without blocking the said receiving channel.

13. The electrosurgical instrument as claimed in claim 12, wherein the lower portion of the grippable member acts as a secondary retainer for the illuminator.

\* \* \* \* \*